United States Patent [19]
Kato et al.

[11] Patent Number: 5,712,138
[45] Date of Patent: Jan. 27, 1998

[54] FRUCTOSYL AMINO ACID OXIDASE

[75] Inventors: Nobuo Kato, Kameoka; Yasuyoshi Sakai, Otsu; Yoshiki Tani, Kyoto; Toshikatsu Sakai, Kyoto; Kaori Ishimaru, Kyoto, all of Japan

[73] Assignee: Kyoto Daiichi Kagaku Co., Ltd., Kyoto-fu, Japan

[21] Appl. No.: 536,190

[22] Filed: Sep. 29, 1995

[30] Foreign Application Priority Data

Oct. 5, 1994 [JP] Japan .................. 6-241556

[51] Int. Cl.$^6$ ................................ C12N 9/02
[52] U.S. Cl. .............. 435/189; 435/191; 435/132
[58] Field of Search .................... 435/189, 191, 435/132

[56] References Cited

U.S. PATENT DOCUMENTS

| | | |
|---|---|---|
| 5,370,990 | 12/1994 | Staniford et al. |
| 5,387,109 | 2/1995 | Ishikawa et al. ............... 435/171 |

FOREIGN PATENT DOCUMENTS

| | | |
|---|---|---|
| 0526150 | 2/1993 | European Pat. Off. |
| 0576838 A2 | 1/1994 | European Pat. Off. |
| 0576838 A3 | 4/1994 | European Pat. Off. |
| 2-195899 | 8/1990 | Japan . |
| 2-195900 | 8/1990 | Japan . |
| 3-155780 | 7/1991 | Japan . |
| 4-4874 | 1/1992 | Japan . |
| 5-33997 | 5/1993 | Japan . |
| 5-192193 | 8/1993 | Japan . |
| 6-46846 | 2/1994 | Japan . |
| 6-65300 | 8/1994 | Japan . |

OTHER PUBLICATIONS

Horiuchi et al., "Purification and Properties of Fructosyl-amino Acid Oxidase from Corynebacterium sp. 2-4-1"; Agricultural and Biological Chemistry; vol. 53, Jan. 1989; pp. 103-111.

Horiuchi et al., "Purification and Properties of Fructosy-lamine Oxidase from Aspergillus sp. 1005"; Agricultural and Biological Chemistry; vol. 55, Feb. 1991; pp. 333-339.

Cole et al., Biological/Biomedical Applications . . . , Chromatogr. Sci. 10: 659 (1979).

Klenk et al., Determination of Glycosylated . . . , Clin. Chem., vol. 28, No. 10, pp. 2088-2094, 1982.

Menard et al., Quantitative Determination . . . , Clin. Chem. vol. 26, No. 11, pp. 1598-1602, 1980.

Homogeneous Immunoturbidimetry of Hemoglobin . . . , JJCLA 18: 620 (1993).

Clinical Application of Serum Glycated Albumin, J. Clin. Lab. Inst. Reag. 16: 33-37 (1993).

Roger N. Johnson et al., Fructosamine: a new approach . . . , Clin. Chim. Acta, 127, pp. 87-95, 1982.

Roswitha Dolhofer et al., Improvement of the thiobarbituric acid . . . , Clin. Chim. Act. 112, pp. 197-204, 1981.

Sangduk Kim et al., Purification and Properties of the Enzyme, J. Biol. Chem., vol. 239, pp. 3790-3796, 1964.

Niggilberg et al., Nonenzymatic Glycosylation of Albumin et al., J. Biol. Chem., 261, pp. 13542-13545, 1986.

H. Franklin Bunn et al., Structural Heterogeneity of Human . . . , J. Biol. Chem. 254, pp. 3892-3898, 1979.

Tatsuo Horiuchi et al., Purification and Properties of . . . , Agric. Biol. Chem., 53(1), pp. 103-110, 1989.

Tatsuo Horiuchi et al., Purification and Properties of . . . , Agric. Biol. Chem., 55(2), pp. 333-358, 1991.

*Primary Examiner*—Blaine Lankford
*Attorney, Agent, or Firm*—Birch, Stewart, Kolasch & Birch, LLP

[57] ABSTRACT

A novel fructosyl amino acid oxidase derived from genus Fusarium, which is active on both of fructosyl lysine and fructosyl valine, a process for producing the enzyme, an assay of an amadori compound using the enzyme, a reagent or a kit containing the enzyme is provided.

3 Claims, 9 Drawing Sheets

FRUCTOSYL AMINO ACID OXIDASE

FIELD OF THE INVENTION

The present invention relates to a novel fructosyl amino acid oxidase. More particularly, it relates to a novel fructosyl amino acid oxidase derived from genus Fusarium, a process for producing the enzyme, an assay of an amadori compound using the enzyme, and a reagent or a kit containing the enzyme.

BACKGROUND OF THE INVENTION

When reactive substances such as protein, peptide and amino acid having an amino group(s) coexist with a reducing sugar such as aldose having an aldehyde group(s), they combine nonenzymatically and irreversibly through the amino and aldehyde groups, which is followed by amadori rearrangement to form an amadori compound. The production rate of an amadori compound being a function of concentration of reactants, period of contact, temperature and the like, various useful information about a sample containing such a reactive substance(s) can be derived from the amount of amadori compounds. Examples of materials containing an amadori compound include food products such as soy sauce and body fluids such as blood.

In a living body, fructosylamines are formed through the reaction between glucose and an amino acid, and the resultant glycated derivatives of hemoglobin, albumin and proteins in blood are called glycohemoglobin, glycoalbumin and fructosamine, respectively. As the concentration of these glycated derivatives in blood reflects an average of blood sugar levels over a particular period of time, it can be used as a significant index for diagnosis and control of conditions of diabetes. Therefore, the establishment of a method of measuring an amadori compound in blood is clinically useful.

Further, a state of preservation and period after production of a food product can be estimated on the basis of the amount of amadori compounds in the food product. Therefore, the method of measuring an amadori compound can also contribute to the quality control of a food product.

Thus, an assay of amadori compounds should be useful in wide range of fields involving medicine and food products.

As assay of amadori compounds, there has been known method which utilizes high performance liquid chromatography [Chromatogr. Sci. 10:659 (1979)], a column filled with solid materials to which boric acid is attached [Clin. Chem. 28:2088–2094 (1982)], electrophoresis [Clin. Chem. 26:1598–1602 (1980)] or antigen-antibody reaction [JJCLA 18:620 (1993), J. Clin. Lab. Inst. Reag. 16:33–37 (1993)], a method for measuring the amount of fructosamine [Clin. Chim. Acta 127:87–95 (1982)], a colorimetric determination following the oxidization with thiobarbituric acid [Clin. Chim. Acta 112:197–204 (1981)], or the like. The existing methods, however, require an expensive device(s) and are not necessarily accurate and rapid enough.

In the field of clinical assay and food analysis, a method utilizing enzymatic process has recently been widely used, because, owing to characteristics of enzymes (specificity in terms of substrate, reaction, structure, active site, etc.), an intended substance can be selectively analyzed with accuracy and rapidity.

There have already been proposed assays which comprise reacting an oxidoreductase with amadori compounds and determining oxygen consumption or hydrogen peroxide generation as an index of the amount of amadori compounds (e.g. Japanese Patent Publication (KOKOKU) Nos. 5-33997 and 6-65300, and Japanese Laid-Open Patent Publication Nos. 2-195900, 3-155780, 4-4874, 5-192193 and 6-46846). Further, assays of glycated protein for the diagnosis of diabetes have been disclosed (Japanese Laid-Open Patent Publication Nos. 2-195899, 2-195900, 5-192193 and 6-46846).

The decomposition of amadori compounds catalyzed by an oxidoreductase can be represented by the following reaction scheme:

wherein $R^1$ is an aldose residue and $R^2$ is an amino acid, protein or peptide residue.

Examples of enzymes which catalyze the above reaction are as follows:

1. fructosyl amino acid oxidase derived from Corynebacterium (Japanese Patent Publication Nos. 5-33997 and 6-65300) or Asperqillus (Japanese Laid-Open Patent Publication No. 3-155780)];

2. fructosylamine deglycase derived from Candida (Japanese Laid-Open Patent Publication No. 6-46846);

3. fructosyl amino acid deglycase derived from Penicillium (Japanese Laid-Open Patent Publication No. 4-4874);

4. ketoamine oxidase derived from Corynebacterium, Fusarium, Acremonium or Debaryomyces (Japanese Laid-Open Patent Publication No. 5-192193)]; and 5. alkyllysinase which can be prepared according to the method described in J. Biol. Chem., Vol. 239, pp. 3790–3796 (1964).

Assays involving these existing enzymes, however, had some drawbacks.

For instance, a glycated protein in blood which serves as an index for the diagnosis of diabetes is a glycated albumin, a glycated hemoglobin and a fructosamine. A glycated albumin is formed when glucose is bound to a lysine residue at its □-position on protein molecule [J. Biol. Chem., 261:13542–13545 (1986)]. In the case of glycated hemoglobin, glucose is also bound to N-terminal valine of β-chain [J. Biol. Chem. 254:3892–3898 (1979)]. Therefore, it is necessary to use an enzyme highly specific to fructosyl valine as well as fructosyl lysine to conduct the determination of glycated proteins as an index of diabetes efficiently. However, the existing enzyme derived from Corynebacterium does not act on fructosyl lysine. As for an enzyme from Aspergillus, its action on glycated proteins or hydrolyzed products thereof is unclear. Although the ketoamine oxidase described in Japanese Laid-Open Patent Publication No. 5-192193 reacts on fructosyl valine, it does not afford an accurate assay of glycated proteins where a lysine residue is bound to a sugar. Because the fructosylamine deglycase is highly specific to difructosyl lysine, it is not available in an assay specific to a substance in which a lysine residue being glycated at the ε-position or that in which valine residue is glycated. Furthermore, a method using an alkyllysinase cannot be reliable and accurate because said enzyme lacks in specificity and reacts with substances in which lysine residue is bonded to a moiety other than sugar. Fructosyl amino acid deglycase derived from Penicillium (Japanese Laid-Open Patent Publication No. 4-4874) reacts on both of fructosyl lysine and fructosyl alanine not valine.

As described above, existing enzymes cannot necessarily give an accurate assay of glycated proteins and therefore the development of an enzyme highly specific to fructosyl lysine and fructosyl valine has been demanded.

In general, for the improvement of accuracy and usefulness of an assay involving an enzymatic process, it is essential to use an enzyme having a catalytic activity suitable for purposes of a given assay. Thus, it is necessary to select an appropriate enzyme taking many factors such as a substance to be determined, as a substrate of the enzyme, the condition of a sample, measuring conditions and the like into consideration in order to carry out the assay with accuracy and reproducibility. To select a suitable enzyme, many enzymes must be previously obtained and characterized regarding the activity, substrate specificity, temperature stability, pH stability and the like. Therefore, it is necessary to develop more and more fructosyl amino acid oxidases and characterize the same.

SUMMARY OF THE INVENTION

The present inventors have intensively studied for purposes of providing a novel fructosyl amino acid oxidase specific to amadori compounds, particularly to glycated protein, and have found that objective enzymes can be obtained by culturing a strain of Fusarium in the presence of fructosyl lysine and/or fructosyl $N^\alpha$-Z-lysine.

Thus, the present invention provides a novel fructosyl amino acid oxidase, which is active on both of fructosyl lysine and fructosyl valine, and which is produced by culturing a strain of Fusarium capable of producing a fructosyl amino acid oxidase in a medium containing fructosyl lysine and/or fructosyl $N^\alpha$-Z-lysine.

DETAILED DESCRIPTION OF THE INVENTION

For purposes of the present invention, a medium containing fructosyl lysine contains fructosyl lysine and/or fructosyl $N^\alpha$-Z-lysine, which is used for culturing a microorganism capable of producing a fructosyl amino acid oxidase of the present invention, which comprises fructosyl lysine and/or fructosyl $N^\alpha$-Z-lysine (hereinafter, it may be abbreviated as "FZL") obtained by autoclaving glucose together with lysine and/or $N^\alpha$-Z-lysine at 100° to 150° C. for 3 to 60 minutes. As is hereinafter described, the fructosyl amino acid oxidase of the present invention is unexpectedly specific to both of fructosyl lysine including FZL and fructosyl valine, where the activity to the former is the same or greater than that to the latter. Throughout the specification, the term "fructosyl amino acid oxidase" of the present invention may be abbreviated as "FAOD".

The enzyme of the present invention can be prepared by culturing a strain of *Fusarium* capable of producing FAOD in a medium containing fructosyl lysine and/or FZL.

Examples of strains of *Fusarium* include those of *Fusarium oxysporum* f. sp. lini (IFO No. 5880) FERM BP-5792, *Fusarium oxysporum* f. sp. batatas (IFO No. 4468), *Fusarium oxysporum* f. sp. niveum (IFO No. 4471), *Fusarium oxysporum* f. sp. cucumerinum (IFO No. 6384), *Fusarium oxysporum* f. sp. melongenae (IFO No. 7706), *Fusarium oxysporum* f. sp. apii (IFO No. 9964), *Fusarium oxysporum* f. sp. pini (IFO No. 9971) and *Fusarium oxysporum* f. sp. fragariae (IFO No. 31180).

A preferred strain of *Fusarium oxysporum* f.sp. lini has been deposited at the National Institute for Bioscience and Human Technology of the Agency of Industrial Technology, 1-3 Higashi 1 Chome, Tsukuba-Shi, Ibararki-ken 305, Japan, on Jan. 23, 1997, under the terms and conditions of the Budapest Treaty, under the accession number FERM BP-5792.

FAODs of the present invention generally have the following physicochemical characteristics:

1) they catalyze the oxidation of an amadori compound in the presence of oxygen to generate α-ketoaldehyde, amine derivatives and hydrogen peroxide;

2) they are stable in the pH range of about 4.0 to 13.0 with an optimal pH of 8.5;

3) they are stable in the temperature range of about 20° to 50° C. with an optimal temperature of 30° to 35° C.; and 4) the molecular weight is about 106,000 (106 kDa) when estimated by gel filtration with Superdex 200 pg.

Fructosyl lysine and/or FZL used for the preparation of FAOD of the present invention can be obtained by autoclaving 0.01 to 50% (w/w) glucose together with 0.01 to 20% (w/w) lysine and/or $N^\alpha$-Z-lysine in a solution at 100° to 150° C. for 3 to 60 minutes. Specifically, it is prepared by autoclaving a solution containing, in a total volume of 1000 ml, 200 g of glucose and 10 g of $N^\alpha$-Z-lysine at 120° C. for 20 minutes.

A medium containing fructosyl lysine and/or FZL (said medium may be referred to as FZL-medium) can be obtained by adding fructosyl lysine and/or FZL obtained in a manner described above to any one of conventional media, but it can be conveniently prepared by autoclaving a mixture (preferably, pH 5.6 to 6.0) comprising 0.01 to 50% (w/w) glucose, 0.01 to 20% (w/w) lysine and/or $N^\alpha$-Z-lysine, 0.1% (w/w) $K_2HPO_4$, 0.1% (w/w) $NaH_2PO_4$, 0.05% (w/w) $MgSO_4 \cdot 7H_2O$, 0.01% (w/w) $CaCl_2 \cdot 2H_2O$ and 0.2% (w/w) yeast extract at 100° to 150° C. for 3 to 60 minutes.

The medium usable for the production of FAOD of the present invention can be a synthetic or natural medium which is generally used in the art and contains a carbon source, nitrogen source, inorganic substance and other nutrients. Examples of carbon source include glucose, xylose, glycerin and the like; examples of nitrogen source include peptone, casein digest, yeast extract, and the like; and examples of inorganic substance include sodium, potassium, calcium, manganese, magnesium, cobalt, and the like which are usually contained in a normal medium.

FAOD of the present invention can be induced to the highest extent when a microorganism is cultured in a medium containing fructosyl lysine and/or FZL. Examples of preferred medium include fructosyl lysine—and/or FZL-containing medium (1.0% glucose, 0.5% fructosyl lysine and/or FZL, 1.0% $K_2HPO_4$, 0.1% $NaH_2PO_4$, 0.05% $MgSO_4 \cdot 7H_2O$, 0.01% $CaCl_2 \cdot 2H_2O$ and 0.01% vitamin mixture), in which fructosyl lysine and/or FZL is used as the sole nitrogen source and glucose as the carbon source.

A medium (pH 5.6 to 6.0) containing 20 g (2%) of glucose, 10 g (1%) of fructosyl lysine and/or FZL, 1.0 g (0.1%) of $K_2HPO_4$, 1.0 g (0.1%) of $NaH_2PO_4$, 0.5 g (0.05%) of $MgSO_4 \cdot 7H_2O$, 0.1 g (0.01%) of $CaCl_2 \cdot 2H_2O$ and 2.0 g (0.2%) of yeast extract in 1,000 ml of a total volume is especially preferred.

The medium containing fructosyl lysine and/or FZL can be prepared by adding fructosyl lysine and/or FZL to any of conventional medium, or by autoclaving a medium containing glucose together with lysine and/or $N^\alpha$-Z-lysine. The medium obtained by either method is colored brown owing to the presence of fructosyl lysine and/or FZL and is therefore referred to as "FZL brown-colored medium or GL (glycated lysine and/or glycated $N^\alpha$-Z-lysine) brown-colored medium".

Figure 1:
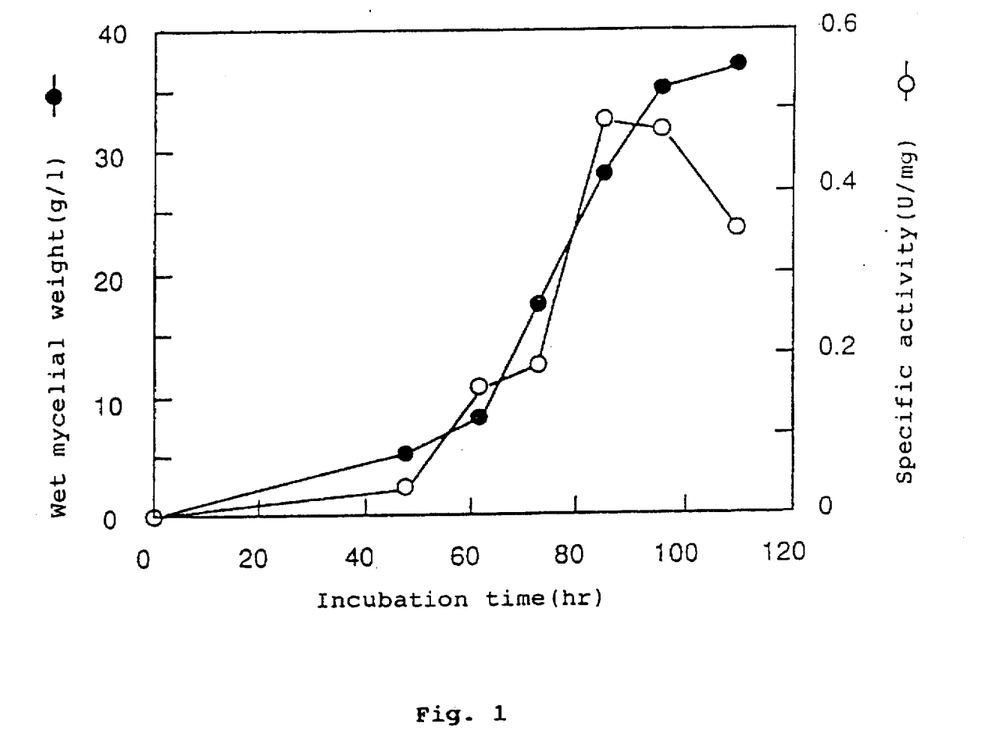
FIG. 1 is a graph illustrating a relation between the cultivation time and the amount of FAOD produced in a culture medium.

The cultivation is normally conducted at temperature range of 25° to 37° C., preferably at 28° C. in a medium of pH range of 4.0 to 8.0, preferably 5.5 to 6.0. However, the culturing conditions may vary depending on various factors such as conditions of microorganisms and should not be limited to those described above. For instance, *Fusarium oxysporum* f. sp lini, when cultured for 20 to 100 hours, preferably 80 hours under these conditions, FAOD is accumulated in the culture medium (see, FIG. 1).

The resultant culture medium is then treated in a conventional manner to remove nucleic acids, cell wall fragments and the like to yield an enzyme preparation.

Since the enzyme activity of FAODs of the present invention are normally accumulated in bacterial/fungal cells, cells in the culture are harvested and ground extract the enzyme.

The grinding of cells can be carried out in a conventional manner, for example, by means of mechanical grinding, autodigestion using a solvent, freezing, ultrasonic treatment, pressurization, or the like.

The method of isolation and purification of an enzyme is also known in the art. It can be conducted by combining known methods such as salting-out with ammonium sulfate, precipitation with an organic solvent such as ethanol, etc., ion-exchange chromatography, hydrophobic chromatography, gel filtration, affinity chromatography, and the like.

For example, mycelia are harvested by subjecting the resultant culture to centrifugation or suction filtration, washed, suspended in 0.1 M Tris-HCl buffer (pH 8.5), ground with Dino-Mill and centrifuged. The supernatant as cell-free extract is then fractionated with ammonium sulfate and purified by subjecting to the phenyl-Sepharose hydrophobic column chromatography.

For purposes of the present invention, FAOD includes any enzyme-containing substances and solutions obtainable throughout the total purification process irrespective of the purity of the enzyme, including the cultured medium as far as the substances and solutions have the ability to catalyze the oxidization of amadori compounds as defined above.

Further, any fragments of FAOD which are associated to the enzymatic activity of FAOD and maintain the same also fall within the scope of the invention because such fragments are also useful for purposes of the present invention.

FAOD thus obtained is useful for the determination of amadori compounds, particularly, that of glycated proteins in the diagnosis of diabetes.

Accordingly, the present invention provides a process for producing FAOD, which comprises culturing a strain of fungi in a medium containing a glycated amino acid and/or glycated protein which are optionally protected.

The present invention also provides a process for producing FAOD, which comprises culturing a strain of Fusarium capable of producing FAOD in a medium containing fructosyl lysine and/or fructosyl $N^{\alpha}$-Z-lysine and recovering FAOD from the resulting culture.

All FAODs produced by strains of *Fusarium* are useful to solve the problems to be solved by the present invention. In the present specification, FAOD produced by *Fusarium oxysporum* f. sp. lini may be referred to as FAOD-L as the occasion demands.

FAODs of the present invention have the following characteristics:

1. Normal induction characteristics

FAOD of the present invention is an inducible enzyme induced by fructosyl lysine and/or FZL and is produced by culturing a strain of *Fusarium* capable of producing FAOD in a medium containing fructosyl lysine and/or FZL as the nitrogen source and glucose as the carbon source. FAOD can be induced in a GL brown-colored medium obtained by autoclaving glucose together with lysine and/or $N^{\alpha}$-Z-lysine but not in a medium containing glucose and lysine and/or $N^{\alpha}$-Z-lysine which are autoclaved separately, which indicates that the enzyme is specific to amadori compounds.

2. Reaction specificity and substrate specificity

FAOD of the present invention has a catalytic activity in the reaction represented by the scheme:

$R^1$—CO—$CH_2$—NH—$R^2$ + $O_2$ + $H_2O$ → $R^1$—CO—CHO + $R^2$—$NH_2$ + $H_2O_2$ wherein $R^1$ is an aldose residue and $R^2$ is an amino acid, protein or peptide residue.

In the above reaction scheme, amadori compounds of the formula $R^1$—CO—$CH_2$—NH—$R^2$ wherein $R^1$ is —OH, —$(CH_2)_n$— or —$[CH(OH)]_n$—$CH_2OH$ (n is an integer of 0 to 6) and $R^2$ is —$CHR^3$—$[CONHR^3]_m$COOH ($R^3$ is a side chain residue of an α-amino acid and m is an integer of 1 to 480) are preferred as substrate. Among them, compounds wherein $R^3$ is a side chain residue of an amino acid selected from lysine, polylysine, valine, asparagine, etc., n is 5 to 6 and m is 55 or less are more preferred.

Substrate specificity of FAOD in the present invention is shown in Table 1 below.

TABLE 1

Substrate specificity of purified FAOD-L

| Substrate | Concentration | Specific activity (%) |
|---|---|---|
| $N^{\epsilon}$-Fructosyl $N^{\alpha}$-Z-lysine | 1.67 mM | 100 |
| Fructosyl valine | 1.67 | 30.1 |
| $N^{\epsilon}$-methyl-L-lysine | 1.67 | N.D.*1 |
| $N^{\epsilon}$-Fructosyl poly-L-lysine | 0.02% | 0.24 |
| Poly-L-Lysine | 0.02 | N.D. |
| F B S A*2 | 0.17 | N.D. |
| F H S A*3 | 0.17 | N.D. |
| Tryptic FBSA | 0.17 | 0.62 |
| Tryptic FHSA | 0.17 | N.D. |

*1 not detected
*2 fructosyl bovine serum albumin
*3 fructosyl human serum albumin As is apparent from Table 1, FAOD of the present invention is highly specific to both of FZL and fructosyl valine. FAOD is active on fructosyl poly-lysine and protease-digestion products of glycated protein.

Examples of FAOD-producing strains of *Fusarium* are shown in Table 2 below.

TABLE 2

Substrate specificity of FAODs purified from strains of Fusarium grown in FZL brown-colored medium

| IFO No. | F. oxysporum f. sp. | Specific activity Fructosyl $N^{\alpha}$-Z-lysine | ($10^{-2}$U/mg protein) Fructosyl valine | L/V[1) |
|---|---|---|---|---|
| 4468 | batatas | 3.76 | 0.228 | 16.5 |
| 4471 | niveum | 3.37 | 0.340 | 9.9 |
| 5880 | lini | 48.6 | 13.5 | 3.6 |
| 6384 | cucumerinum | 2.26 | 0.234 | 9.7 |
| 7706 | melongenae | 4.86 | 0.276 | 17.6 |
| 9964 | apii | 2.65 | 0.169 | 15.7 |
| 9971 | pini | 1.92 | 0.138 | 13.9 |
| 31180 | fragariae | 25.2 | 2.27 | 11.1 |

1)(activity on FZL)/(activity on fructosyl valine)

As is apparent from Table 2, FAODs of the present invention are active on both of fructosyl lysine and fructosyl valine, which indicates that the said FAOD is useful for analysis of glycated hemoglobin too.

3. pH and Temperature conditions
Measurement of pH condition:

The optimal pH is determined by carrying out the enzyme reaction in a conventional reaction system for determination of FAOD activity, e.g. those shown in "4. Evaluation of titer" below, utilizing various buffers of pH 4 to 13 such as 0.1 M potassium phosphate buffer (KPB), Tris-HCl buffer, glycine (Gly)—NaOH buffer and the like instead of usual buffer.

The pH stability was determined by adding FAOD to various buffers described above and measuring the activity of FAOD under a normal condition (30° C., pH 8.0) after incubating for 10 minutes at 30° C.

Measurement of temperature condition

The optimal temperature is determined by carrying out the reaction at various temperature from 20° to 60° C. and measuring the enzyme activity. The temperature stability was determined as remaining activity in enzyme solutions under normal conditions, which solutions have been prepared by dissolving FAOD in 0.1M Tris-HCl buffer (pH 8.0) and incubating at various temperature ranging from 20° to 60° C. for 10 minutes.

Figure 2:
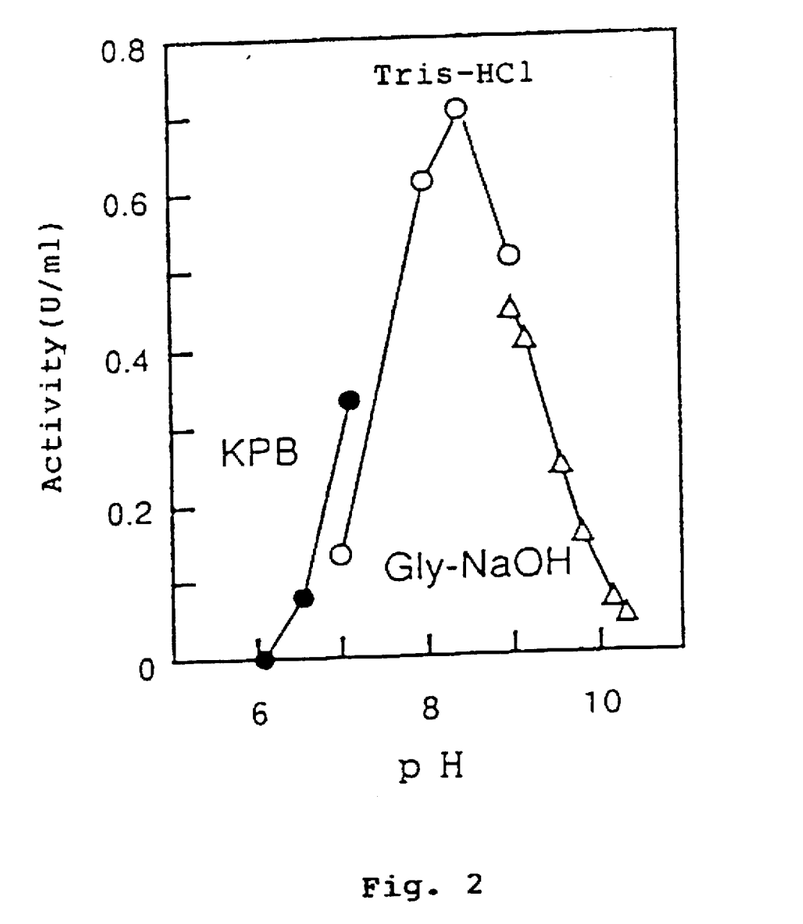
FIG. 2 is a graph illustrating a relation between the pH and the activity of FAOD in a solvent.

FAOD of the present invention, when evaluated according to these methods, is stable in the pH range of 4.0 to 13.0. The optimal pH is between 7.5 and 9.0, preferably 8.5 (see, FIG. 2).

Figure 3:
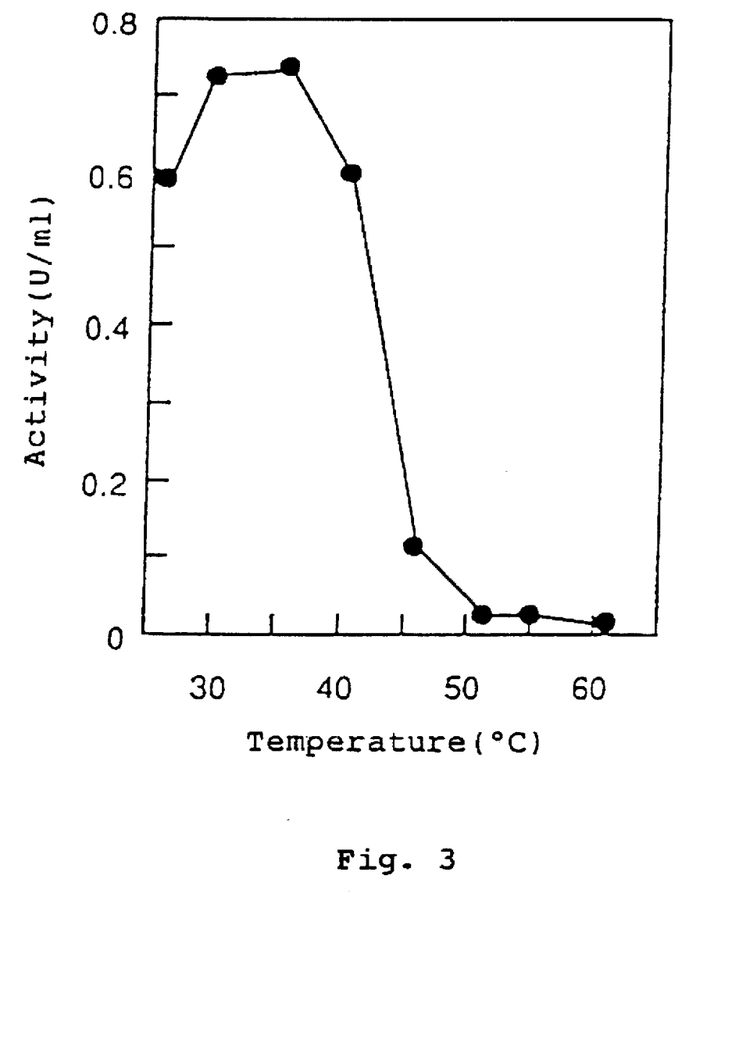
FIG. 3 is a graph illustrating a relation between the temperature and the activity of FAOD in a solvent.

The enzyme reaction proceeds efficiently at 20° to 50° C., preferably 25° to 40° C., more preferably 35° C. (see, FIG. 3). FAOD of the present invention is stable at temperature range of 20° to 50° C.

4. Evaluation of titer

Titration was carried out as follows:

(1) Method utilizing colorimetric determination of generated hydrogen peroxide

A. Measurement of generation rate.

A 100 mM FZL solution was prepared by dissolving previously-obtained FZL in distilled water. To a mixture of 100 µl of 45 mM 4-aminoantipyrine, 100 µl of peroxidase (60 U/ml), 100 µl of 60 mM phenol, 1 ml of 0.1 M Tris-HCl buffer (pH 8.0) and 50 µl of enzyme solution was added distilled water to give a total volume of 3.0 ml. The solution was incubated for 2 minutes at 30° C. After adding 50 µl of 100 mM FZL solution, the time course of absorbance at 505 nm was measured. The amount (µmol) of hydrogen peroxide generated per minute was calculated on the basis of molar absorptivity ($5.16 \times 10^3$ $M^{-1}cm^{-1}$) of quinone pigment produced. The resultant numerical value was taken as a unit(U) of enzyme activity.

B. End point method

According to the same manner as that described in the method A above, a solution was prepared and a substrate solution was added thereto. After 30 minutes of incubation at 30° C., absorbance at 505 nm was measured. The enzyme activity was evaluated on the basis of the amount of hydrogen peroxide generated referring to a calibration curve previously obtained using a standard hydrogen peroxide solution.

(2) Method of determination of oxygen absorption due to enzyme reaction

To a mixture of 1 ml of 0.1 M Tris-HCl buffer (pH 8.0) and 50 µl of an enzyme solution was added distilled water to obtain a solution of a total volume of 3.0 ml. The resulting solution was charged in a cell of an oxygen electrode manufactured by Lank Brothers Co. The solution was stirred at 30° C. to allow the dissolved oxygen to be equilibrated under the temperature and 100 µl of 50 mM FZL was added to it. Then, the oxygen absorption was continuously measured on a recorder to obtain an initial rate. The amount of oxygen absorbed for one minute was determined on the basis of a calibration curve, which was taken as an enzyme unit.

5. Inhibition, activation and stabilization of enzyme (1) Effect of metal

To an enzyme solution was added a solution containing a metal ion to be tested at a final concentration of 1 mM in 0.1 M Tris-HCl buffer (pH 8.0). After 5 minutes of incubation at 30° C., the enzyme activity was evaluated. The results are shown in Table 3 below.

TABLE 3

Effect of metal ion on the activity of FAOD-L

| Metal (1 mM) | Specific activity (%) | Metal (1 mM) | Specific activity (%) |
|---|---|---|---|
| None | 100 | $FeSO_4$ | 93 |
| LiCl | 99 | $CoSO_4$ | 110 |
| KCl | 104 | $CuCl_2$ | 35 |
| NaCl | 109 | $ZnSO_4$ | 11 |
| RbCl | 109 | $AgNO_3$ | 0 |
| CsCl | 108 | $BaCl_2$ | 116 |
| $MgCl_2$ | 103 | $HgCl_2$ | 0 |
| $CaCl_2$ | 98 | $FeCl_3$ | 77 |
| $MnCl_2$ | 143 | | |

As is apparent from Table 3, the activity of FAOD of the present invention is slightly inhibited by copper and zinc ions and is completely inhibited by silver and mercury ions.

(2) Effect of various inhibitors

The inhibitory effect of various substances was tested in a manner substantially analogous to that described in (1) above. In the present test, the final concentration of PCMB (parachloro mercuric benzoate) is 0.1 mM while that of others 1 mM. The results are shown in Table 4. The stabilization effect was examined by dialyzing the purified FAOD overnight against 50 mM Tris-HCl buffer (pH 8.5) containing 2 mM dithiothreitol (DTT) and measuring the enzyme activity.

TABLE 4

Effect of various inhibitors on activity of FAOD

| Reagent (1 mM) | Specific activity (%) | Reagent (1 mM) | Specific activity (%) |
|---|---|---|---|
| None | 100 | Semicarbazide | 96 |
| PCMB[1] | 0 | Phenylhydrazine | 49 |
| DTNB[2] | 0 | Hydrazine | 10 |
| Iodoacetic acid | 90 | Hydroxylamine | 17 |
| $NaN_3$ | 102 | Clorgyline | N.D.[3] |
| α, α'-Dipyridyl | 103 | Deprenyl | 104 |
| o-Phenanthroline | 114 | Aminoguanidine | 73 |

[1]PCMB, parachloro mercuric benzoate.
[2]DTNB, 5,5'-Dithiobis(2-nitrobenzoic acid).
[3]not detected.

As is apparent from Table 4, the activity of FAOD is strongly inhibited by PCMB, DTNB, hydrazine and phenylhydrazine, indicating that SH and/or carbonyl group may play an important role in the enzyme reaction.

The enzyme is stabilized by dithiothreitol (DTT), and preferable solvent for the preservation is 50 mM Tris-HCl buffer (pH 8.5) containing 2 mM DTT.

6. Molecular weight

Molecular weight was estimated by SDS-PAGE (sodium dodecyl sulfate polyacrylamide gel electrophoresis) and gel filtration on Superdex 200 pg.

Figure 4:
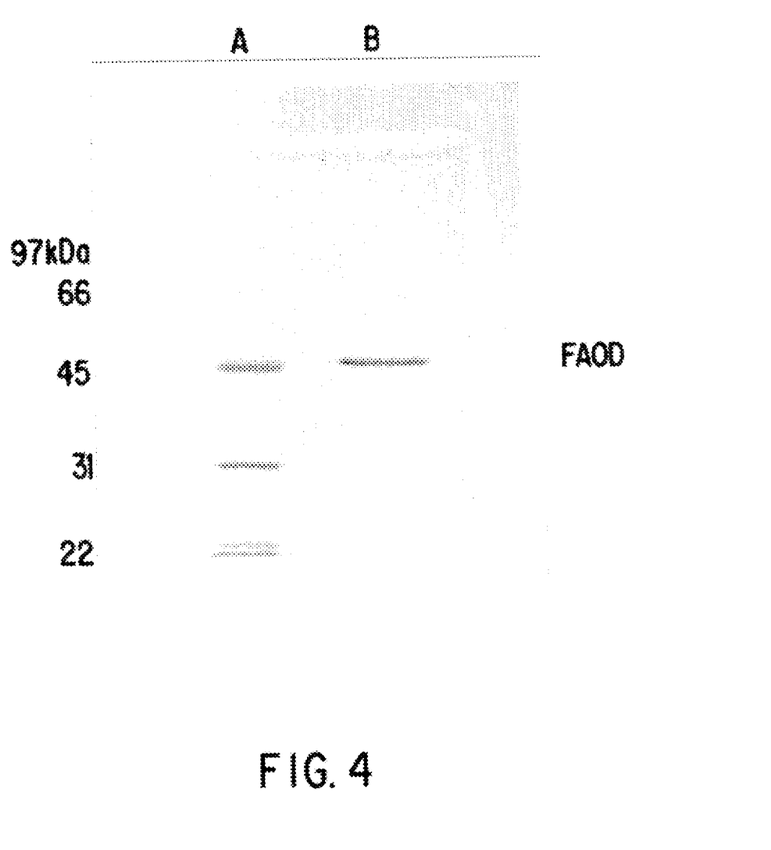
FIG. 4 shows the migration pattern obtained by subjecting purified FAOD-L to SDS-PAGE.

SDS-PAGE was conducted according to the Davis's method using 10% gel at 40 mA for 3 hours and staining protein with Coomassie brilliant blue G-250. Molecular weight was determined on the basis of calibration curve obtained by electrophoresing several standards of known proteins such as phosphorylase B, bovine serum albumin, ovalbumin, carbonic anhydrase and soybean trypsin inhibitor in the same manner. As a result, the molecular weight of a subunit was about 51,000 (51 kDa). (see, FIG. 4)

The gel filtration on Superdex 200 pg revealed that the molecular weight of FAOD to be about 106,000 (106 kDa) (see, FIG. 5), indicating that FAOD of the present invention is a dimer.

7. Isoelectric point

Isoelectric point (pI) of FAOD was 6.8, when measured by disc electrofocusing method.

8. Comparison with known enzymes

FAOD of the present invention was compared with known fructosyl amino acid oxidases derived from various microorganisms.

TABLE 5

Comparison of various fructosyl amino acid oxidases derived from microorganisms

| Microorganism | F. oxysporum f. sp. lini FERM BP-5792 | Corynebacterium sp.[1] | Aspergillus sp.[2] |
|---|---|---|---|
| Molecular weight | | | |
| (gel filtration) | 106,000 | 88,000 | 83,000 |
| (SDS-PAGE) | 51,000 | 44,000 | 43,000 |
| Coenzyme | Covalently-bonded FAD | Noncovalently-bonded FAD | Noncovalently-bonded FAD |
| Substrate specificity (U/mg protein) | | | |
| (Fructosyl lysine) | 18.5[3] | N.D.[4] | 11.28[4] |
| (Fructosyl valine) | 6.83 | 7.09 | 59.8 |
| Michaelis constant | 0.37 mM (FZL) | 0.74 mM (Gly) | 2.2 mM (Gly) |
| Optimum pH | 8.5 | 8.3 | 7.7 |
| Optimum temperature (°C.) | 30–35 | 40 | 40 |
| Isoelectric point | 6.8 | 4.6 | 6.8 |
| Inactivation by SH reagent | Inactivated | not inactivated | Inactivated |

[1] T. Horiuchi et al., Agric. Biol. Chem., 53 (1), 103–110 (1989)
[2] T. Horiuchi et al., Agric. Biol. Chem., 55 (2), 333–338 (1991)
[3] Specific activity to fructosyl $N^\alpha$-Z-lysine
[4] Specific activity to $N^\epsilon$-D-fructosyl $N^\alpha$-formyllysine As is apparent from Table 5, the following differences can be noted between FAOD of the present invention and others derived from two strains.

(1) Molecular weight: FAOD of the present invention is apparently greater than two other enzymes.

(2) Coenzyme: coenzyme for FAOD of the present invention is covalently-bonded FAD, while that for other enzymes is noncovalently-bonded FAD.

(3) Substrate specificity: FAOD of the present invention is more specific to fructosyl lysine compared to fructosyl valine, while the enzyme derived from Corynebacterium does not act on fructosyl lysine, and the one derived from Aspergillus acts on fructosyl lysine only to a lesser extent compared to fructosyl valine.

(4) Michaelis constant: the difference in Michaelis constant indicates that an affinity of FAOD of the present invention to the substrate fructosyl lysine is higher than that of other enzymes.

(5) Optimal pH, optimal temperature, isoelectric point and inhibition by SH reagents: the data indicate that FAOD of the present invention is distinguishable from other enzymes.

As described above, FAOD of the present invention is useful in an assay of amadori compounds.

Accordingly, the present invention provides an assay of an amadori compound in a sample, which comprises bringing the sample containing an amadori compound into contact with FAOD of the present invention and determining the amount of oxygen consumed or that of hydrogen peroxide produced. The assay of the present invention is carried out on the basis of the measurement of the amount of glycated protein and/or glycation rate or the determination of fructosamine in a sample derived from a living body.

The enzyme activity of FAOD is evaluated by the following reaction scheme:

$$R^1-CO-CH_2-NH-R^2+O_2+H_2O \rightarrow R^1-CO-CHO+R^2-NH_2+H_2O_2$$

wherein $R^1$ is an aldose residue and $R^2$ is an amino acid, protein or peptide residue.

As a sample solution to be tested, there can be used any solutions containing an amadori compound(s), for example, those derived from food products such as soy sauce, etc. and from a living body such as blood (e.g. whole blood, plasma or serum), urine, or the like.

FAOD of the present invention is reacted with a sample containing an amadori compound in a suitable buffer. Although the suitable pH and temperature of the reaction mixture may vary depending on the enzyme to be used and the sample to be tested, they can be within the range defined above, that is, at pH 4.0 to 13.0, preferably 8.5 and at temperature from 20° to 50° C., preferably 35° C. As buffer, Tris-HCl buffer can be used.

The amount of FAOD to be used in an assay is normally 0.1 unit/ml or more, preferably 1 to 100 units/ml in the case of end point method.

For purposes of the present invention, the determination of amadori compounds can be carried out by any one of known assays shown below.

(1) Determination based on the amount of hydrogen peroxide generated

The amount of amadori compounds in a sample can be estimated from the amount of hydrogen peroxide produced according to a method for determination of hydrogen peroxide such as colorimetric method or a method utilizing a hydrogen peroxide electrode. The amount of amadori compound in a sample is then estimated on the basis of a calibration curve regarding the relation between the amount of hydrogen peroxide and that of amadori compounds. Specifically, the estimation can be conducted in a manner similar to that described in "4. Evaluation of titer", except that the amount of FAOD is 1 unit/ml and that a sample to be tested is diluted before the measurement of hydrogen peroxide produced.

As the color-developing system for hydrogen peroxide, there can be used any systems which develop color due to oxidative condensation between a chromogen such as phenol and a coupler such as 4-aminoantipyrine, 3-methyl-2-benzothiazolinone hydrazone in the presence of peroxidase. Examples of chromogen include phenolic derivatives, aniline derivatives and toluidine derivatives, for example, N-ethyl-N-(2-hydroxy-3-sulfopropyl)-m-toluidine, N,N-dimethylaniline, N,N-diethylaniline, 2,4-dichlorophenol, N-ethyl-N-(2-hydroxy-3-sulfopropyl)-3,5-dimethoxyaniline, N-ethyl-N-(3-sulfopropyl)-3,5-dimethylaniline, and N-ethyl-N-(2-hydroxy-3-sulfopropyl)-3,5-dimethylaniline. A leuco-type color-developing agent which develops color upon oxidation in the presence of peroxidase is also available. Such "leuco-type color developing agents" are known in the art and examples thereof include o-dianisidine, o-tolidine, 3,3-diaminobenzidine, 3,3, 5,5-tetramethylbenzidine, N-(carboxymethylaminocarbonyl)-4,4-bis(dimethylamino)-biphenylamine, 10-(carboxymethylaminocarbonyl)-3,7-bis(dimethylamino) phenothiazine and the like.

(2) Determination on the basis of the amount of oxygen consumed

Amadori compound in a sample can be estimated from the amount of oxygen consumed which is calculated by subtracting the amount of oxygen at the completion of reaction from the one at the beginning of reaction using a calibration curve concerning the relation of the amount of oxygen consumed and that of amadori compounds. Specifically, it can be conducted in a manner similar to the titration described in "4. Evaluation of titer" above, except that the amount of FAOD is 1 unit/ml and that a sample to be added is previously diluted appropriately before the measurement of oxygen consumed.

According to the assay of the present invention, a sample solution can be used as it is, but it may be preferred in a certain occasion that the sample is pre-treated so as to liberate lysine and/or valine residue to which sugar is bound in a glycated protein.

For such a purpose, the sample is treated with a protease (enzymic method) or a chemical substance such as hydrochloric acid, etc. (chemical method). The enzymic method is preferred. In such a case, proteases of endo—and exo-type known in the art can be used in the process of the present invention. Examples of endo-type protease include trypsin, α-chymotrypsin, subtilisin, proteinase K, papain, cathepsin B, pepsin, thermolysin, protease XIV, lysylendopeptidase, proleser and bromelain F. Examples of exo-type protease include aminopeptidase and carboxypeptidase. The method of the enzyme treatment is also known and, for example, the trypsin treatment can be conducted as described in Examples below.

As described above, FAOD of the present invention is highly specific to fructosyl lysine contained in glycated protein, and thereby being useful in the diagnosis and control of conditions of diabetes, which comprise measuring glycated proteins in blood sample. In another aspect, FAOD of the present invention is specific to fructosyl valine and therefore usable in the assay of glycated hemoglobin.

When blood (e.g. whole blood, plasma or serum) is to be assayed, a blood sample derived from a living body can be used as it is or after pre-treatment such as dialysis, etc.

Further, enzymes (e.g. FAOD, peroxidase, etc.) used in the process of the present invention can be used in a liquid state or after immobilizing to suitable solid supports. For example, a column packed with enzyme immobilized onto beads can be used to obtain an automated device for assay of glycated protein, or the like, which device must improve the efficiency of a routine assay such as clinical examination where a lot of specimens must be tested in accuracy and rapidity. The immobilized enzyme has another advantage in view of economical efficiency because it can be used repeatedly.

Furthermore, it is possible to provide a kit by combining an enzyme(s) with a color-developing reagent(s) in an appropriate manner. Such a kit is useful for both of clinical assay and food analysis of amadori compounds.

The immobilization of the enzyme can be conducted by a method known in the art. For example, it is conducted by a carrier bonding method, cross-linkage method, inclusion method, complexing method, and the like. Examples of carriers include polymer gel, microcapsule, agarose, alginic acid, carrageenan, and the like. The enzyme can be bound to a carrier through covalent bond, ionic bond, physical absorption, biochemical affinity, etc. according to a method known in the art.

When using immobilized enzyme, the assay may be carried out in flow or batch system. As described above, the immobilized enzyme is particularly useful for a routine assay (clinical examination) of glycated proteins in blood samples. When the clinical examination is directed to the diagnosis of diabetes, the result as criterion for diagnosis of diabetes is expressed in fructosamine value, concentration of glycated protein or glycation rate which is the ratio of the concentration of glycated protein to that of whole protein in the sample. The whole protein concentration can be determined in a conventional manner, for example, through the measurement of absorbance at 280 nm, Bradford method, Lowry method, bullet method, natural fluorescence of albumin, or the absorbance of hemoglobin.

The present invention also provides a reagent or a kit used in an assay of amadori compounds, which comprises FAOD of the present invention and a buffer whose pH is preferably 7.5 to 8.5, more preferably 8.0. When FAOD is immobilized, the solid support can be selected from a polymer gel and the like, and alginic acid is preferred.

In the case of end point assay, the reagent usually contains 1 to 100 units/ml of FAOD for a sample, and Tris-HCl buffer (pH 8.0) as a buffer.

When amadori compounds are assayed on the basis of generated hydrogen peroxide, any of the color-developing systems which develop color due to oxidative condensation, leuco-type color-developing agents and the like described in "(1) Determination based on the amount of hydrogen peroxide generated" above can be used.

The reagent used in an assay of amadori compound of the present invention may be combined with a suitable color-developing agent together with a color criterion or a standard substance to give a kit which is useful for a preliminary diagnosis or examination.

The reagent or the kit described above is used for measurement of the amount of glycated protein and/or glycation rate or the determination of fructosamine in a sample derived from a living body.

As is apparent from the description above, FAOD of the present invention is specific to both of fructosyl lysine and fructosyl valine, wherein it is more specific to the former, and differs from existing analogous fructosyl amino acid oxidases in substrate specificity and the like. FAOD of the present invention therefore is useful in the development of novel clinical assays and food analyses. As a result, it can greatly contribute to the diagnosis of diabetes and quality control of food products. In particular, it is useful in a diagnosis of diabetes where the amount of glycated protein and/or glycation rate or fructosamine value in blood is used as an index for diagnosis or control of conditions of diabetes. It is now possible to determine glycated proteins accurately and efficiently by means of assay using a reagent of the present invention for determination of amadori compounds, which facilitates the diagnosis or control of conditions of diabetes.

The following Examples further illustrate the present invention in detail but are not to be construed to limit the scope thereof.

EXAMPLE 1 Fermentation of *Fusarium oxysporum* f. sp. lini and Purification of FAOD-L 1) Fermentation

*Fusarium oxysporum* f. sp. lini (IFO No. 5880) was inoculated into a medium (pH 6.0, 10 L) containing 0.5% FZL, 1.0% glucose, 0.1% $K_2HPO_4$, 0.1% $NaH_2PO_4$, 0.05% $MgSO_4 \cdot 7H_2O$, 0.01% $CaCl_2 \cdot 2H_2O$ and 0.2% yeast extract, and grown at 28° C. for 80 hours with aeration (2 L/min) and stirring (400 rpm) using a jar fermentor. The culture was filtered to harvest mycelia.

2) Preparation of Crude Extract

A portion of mycelia (270 g, wet weight) was suspended in 0.1 M Tris-HCl buffer (pH 8.5, 800 ml) containing 2 mM DTT and ground with Dino-Mill. The ground mixture was centrifuged at 9,500 rpm for 20 minutes to obtain the supernatant (cell-free extract) as a crude extract, which was then subjected to purification.

3) Purification

Step 1: Ammonium Sulfate Fractionation.

To the crude extract was added ammonium sulfate to 40% saturation and the mixture was centrifuged at 12,000 rpm, 4° C. to remove the precipitate. To the supernatant was added ammonium sulfate to 75% saturation and the precipitates were separated.

Step 2: Hydrophobic Chromatography (Batch method)

The precipitates obtained in step 1 above were dissolved in 50 mM Tris-HCl (pH 8.5) containing 2 mM DTT (hereinafter, referred to as "buffer A"). After addition of an equal volume of buffer A containing 40% ammonium sulfate, butyl-Toyopearl resin (200 ml) was added to the solution of crude extract for adsorption. The elution was done by batch method using buffer A. Active fractions were concentrated with ammonium sulfate.

Step 3: Hydrophobic Column Chromatography

The concentrate obtained in step 2 above was adsorbed onto a phenyl-Toyopearl column equilibrated with the buffer A containing 25% saturation of ammonium sulfate. After washing with the same buffer, the elution was done under a linear gradient of 25 to 0% saturation of ammonium sulfate. The active fractions were pooled and concentrated with ammonium sulfate. The resultant concentrate was used in the next step.

Step 4: Hydrophobic Chromatography (Column method)

The concentrate obtained in step 3 above was adsorbed onto a butyl-Toyopearl column equilibrated with the buffer A containing 40% saturation of ammonium sulfate. Column was washed with the same buffer. Active fractions were obtained by eluting with a linear gradient of 40 to 0% saturation of ammonium sulfate.

Step 5: Ion Exchange Column Chromatography

Then, the active fractions obtained in step 4 was applied to DEAE-Toyopearl column equilibrated with the buffer A. FAOD activity was detected in washing fractions, which were pooled and concentrated with ammonium sulfate. The resultant concentrate was used in the next step.

Step 6: Gel Filtration

As the final step, gel filtration was carried out using Sephacryl 300 equilibrated with 0.1M Tris-HCl buffer containing 0.1 M sodium chloride and 2 mM DTT to give an enzyme preparation of 70 to 100 units.

Figure 6:
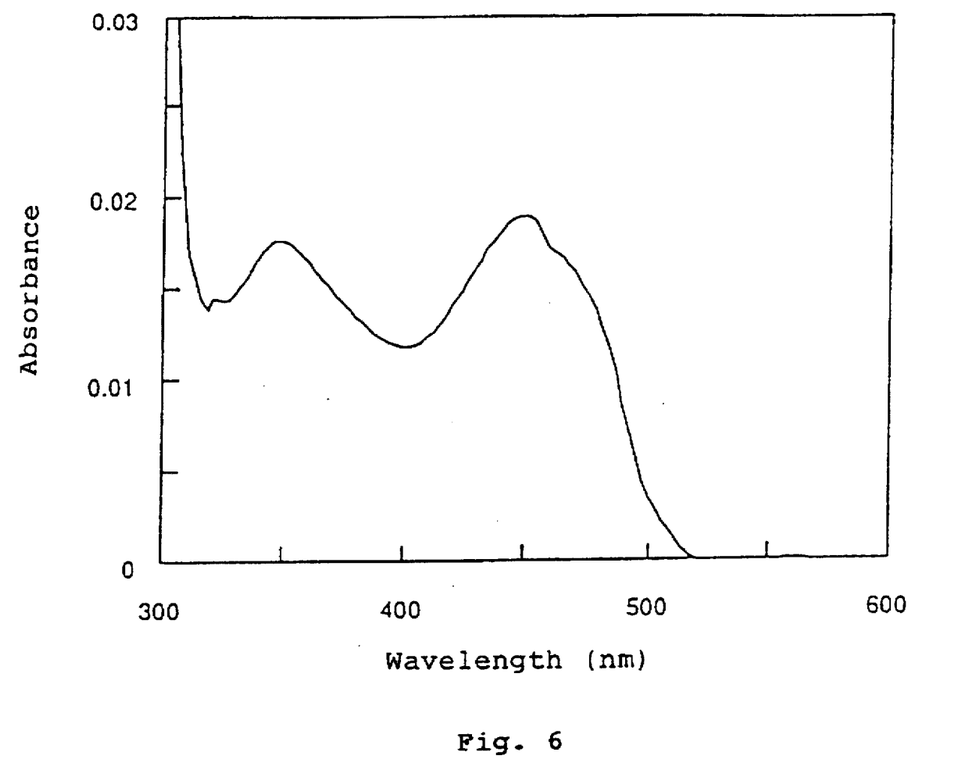
FIG. 6 shows absorption spectrum of a purified FAOD-L.

UV absorption spectrum of the purified enzyme is shown in FIG. 6, which indicates that the enzyme is a flavin enzyme.

The purified enzyme was used for determination of molecular weight by SDS-PAGE (sodium dodecylsulfate polyacrylamide gel electrophoresis) and gel filtration on Superdex 200 pg.

SDS-PAGE was conducted according to the Davis's method using 10% gel at 40 mA for 3 hours. Proteins were stained with Coomassie brilliant blue G-250. Molecular weight was estimated using a calibration curve prepared by electrophoresing standard proteins such as phosphorylase B, bovine serum albumin (BSA), ovalbumin, carbonic anhydrase and soybean trypsin inhibitor under the same conditions. SDS-PAGE revealed that the molecular weight of the purified enzyme subunit is about 51,000 (51 kDa) (see, FIG. 4).

Figure 5:
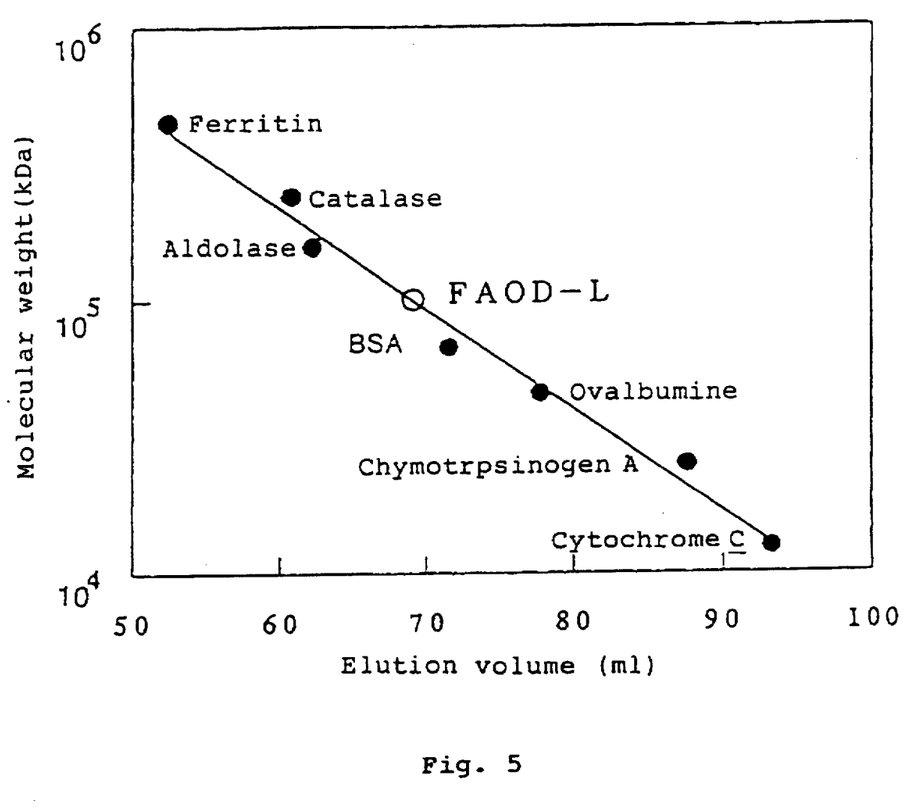
FIG. 5 is a graph showing the measurement of molecular weight of FAOD-L by gel filtration on Superdex 200 pg.

The gel filtration was conducted using 0.1 M Tris-HCl buffer (pH 8.5) containing 0.1 M NaCl, which revealed the molecular weight to be about 106,000 (106 kDa) as shown in FIG. 5.

Furthermore, FAOD-L prepared in Example 1 showed the same values or physicochemical properties in connection with enzyme activity, optimal pH and temperature, pH and temperature stability, effect of metal and inhibitors, etc., as those described above.

EXAMPLE 2 Determination of the Amount of Glycated Human Albumin

A series of glycated human albumin solutions of different concentration between 0 and 10% were prepared by dissolving glycated human serum albumin (Sigma) in 0.9 % sodium chloride solution. The determination was carried out using the solutions in a following manner.

1) Protease Treatment

A mixture of a glycated albumin solution (60 µl) and 12.5 mg/ml protease XIV (Sigma) solution (60 µl) was incubated at 37° C. for 30 minutes. The mixture was then heated at about 90° C. for 5 minutes to stop the reaction.

2) Determination of Activity

FAOD reaction mixture was prepared from the following reagents.

| | |
|---|---|
| 45 mM 4-Aminoantipyrine solution | 30 µl |
| 60 mM N-ethyl-N-(2-hydroxy-3-sulfopropyl)-m-toluidine solution | 30 µl |
| Peroxidase solution (60 units/ml) | 30 µl |
| 0.1 M Tris-HCl buffer (pH 8.0) | 300 µl |
| FAOD-L solution (6 units/ml) | 50 µl |

Figure 7:
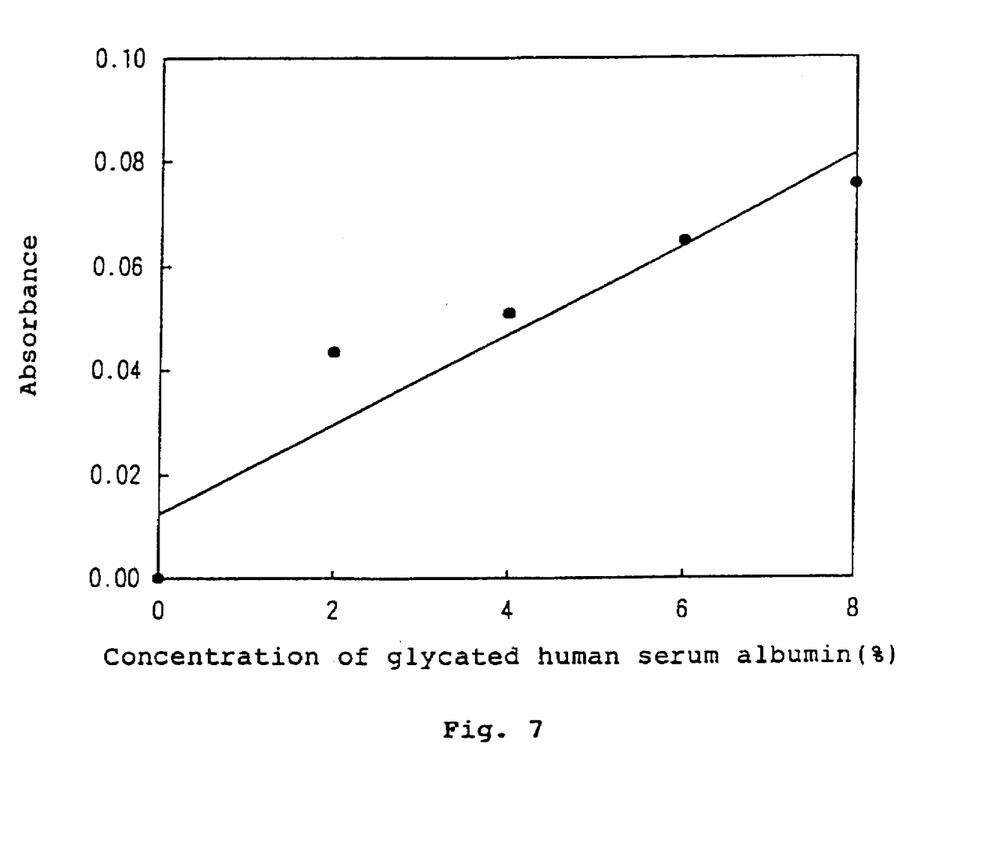
FIG. 7 is a graph illustrating a relation between the concentration of glycated human serum albumin as a substrate and the amount of hydrogen peroxide produced due to FAOD action.

After combining the reagents, the total volume was adjusted to 1 ml with distilled water. FAOD-L solution (6 units/ml) was prepared by diluting the purified FAOD-L obtained in Example 1 with 0.1 M Tris-HCl buffer (pH 8.0). After incubating FAOD reaction mixture at 30° C. for 2 minutes, each of protease-treated solution (100 μl) was added thereto. Then, the absorbance at 555 nm after 30 minutes was measured to evaluate the relationships between the concentration of glycated albumin and absorbance. The results are shown in FIG. 7, wherein the ordinate indicates the absorbance at 555 nm which corresponds to the amount of hydrogen peroxide generated and the abscissa indicates the concentration of glycated albumin. FIG. 7 shows that the concentration of the glycated albumin and the amount of hydrogen peroxide are correlated.

EXAMPLE 3 Measurement of Glycation Rate of Human Serum Albumin

Glycated human serum albumin (Sigma Co.) (150 mg) and human serum albumin (Sigma Co.) (150 mg) were separately dissolved in 0.9% sodium chloride solution (3 ml). These solutions were combined to prepare solutions of different glycation rate and the rate assay was carried out using an automatic glycoalbumin measuring device (Kyoto Daiichi Kagaku Co. Ltd.). The measurement revealed that the glycation rate is from 24.6 to 61.1%. The determination was carried out using these solutions in a following manner.

1) Protease Treatment

A mixture of a glycated albumin solution (60 μl) and 12.5 mg/ml protease XIV (Sigma) solution (60 μl) was incubated at 37° C. for 30 minutes. The mixture was then heated at about 90° C. for 5 minutes to stop the reaction.

2) Determination of Activity

FAOD reaction mixture was prepared from the following reagents.

| | |
|---|---|
| 45 mM 4-Aminoantipyrine solution | 30 μl |
| 60 mM N-ethyl-N-(2-hydroxy-3-sulfopropyl)-m-toluidine solution | 30 μl |
| Peroxidase solution (60 units/ml) | 30 μl |
| 0.1 M Tris-HCl buffer (pH 8.0) | 300 μl |
| FAOD-L solution (6 units/ml) | 50 μl |

Figure 8:
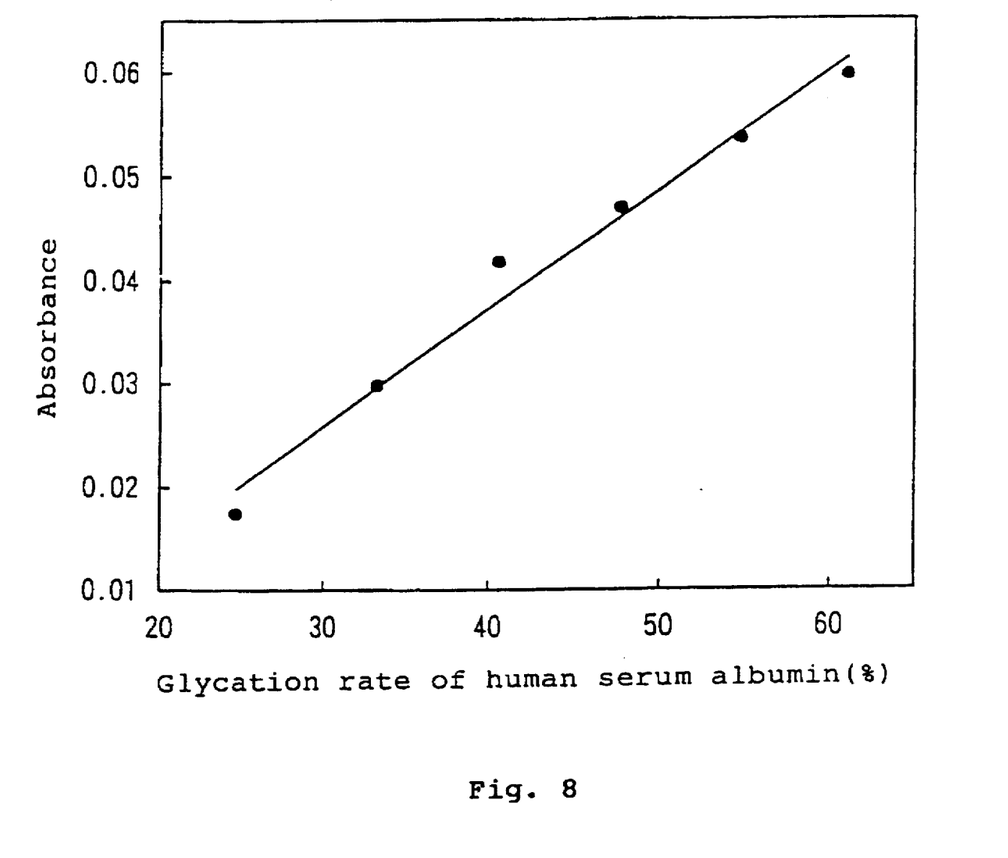
FIG. 8 is a graph illustrating a relation between the glycation rate of human serum albumin and the amount of hydrogen peroxide produced due to FAOD action.

After combining the reagents, the total volume was adjusted to 1 ml with distilled water. FAOD-L solution (6 units/ml) was prepared by diluting the purified FAOD-L obtained in Example 1 with 0.1 M Tris-HCl buffer (pH 8.0). After incubating FAOD reaction mixture at 30° C. for 2 minutes, each of protease-treated solution (100 μl) was added thereto. Then, the absorbance at 555 nm after 30 minutes was measured to evaluate the relationships between the glycation rate of albumin and absorbance. The results are shown in FIG. 8, wherein the ordinate indicates the absorbance at 555 nm which corresponds to the amount of hydrogen peroxide generated and the abscissa indicates the glycation rate. FIG. 8 shows that the glycation rate of albumin and the amount of hydrogen peroxide are correlated.

EXAMPLE 4 Determination of Glycated Hemoglobin Level

A series of glycated hemoglobin solutions of different concentrations between 0 and 30% were prepared by dissolving glycohemoglobin control (Sigma) in distilled water. The determination was carried out using these solutions in a following manner.

1) Protease Treatment

A mixture of a glycated hemoglobin solution (25 μl), 500 units/ml aminopeptidase solution (5 μl) and 0.1 M Tris-HCl buffer (pH 8.0) was incubated at 30° C. for 30 minutes. To the mixture was added 10% trichloroacetic acid (50 μl) and stirred. After allowing to stand for 30 minutes at 0° C., the mixture was centrifuged at 12000 rpm for 10 minutes. The supernatant was neutralized with about 50 μl of 2M NaOH.

2) Determination of Activity

FAOD reaction mixture was prepared from the following reagents.

| | |
|---|---|
| 3 mM N-(carboxymethylaminocarbonyl)-4,4-bis(dimethylamino)biphenylamine solution | 30 μl |
| Peroxidase solution (60 units/ml) | 30 μl |
| 0.1 M Tris-HCl buffer (pH 8.0) | 300 μl |
| FAOD-L solution (4 units/ml) | 10 μl |

Figure 9:
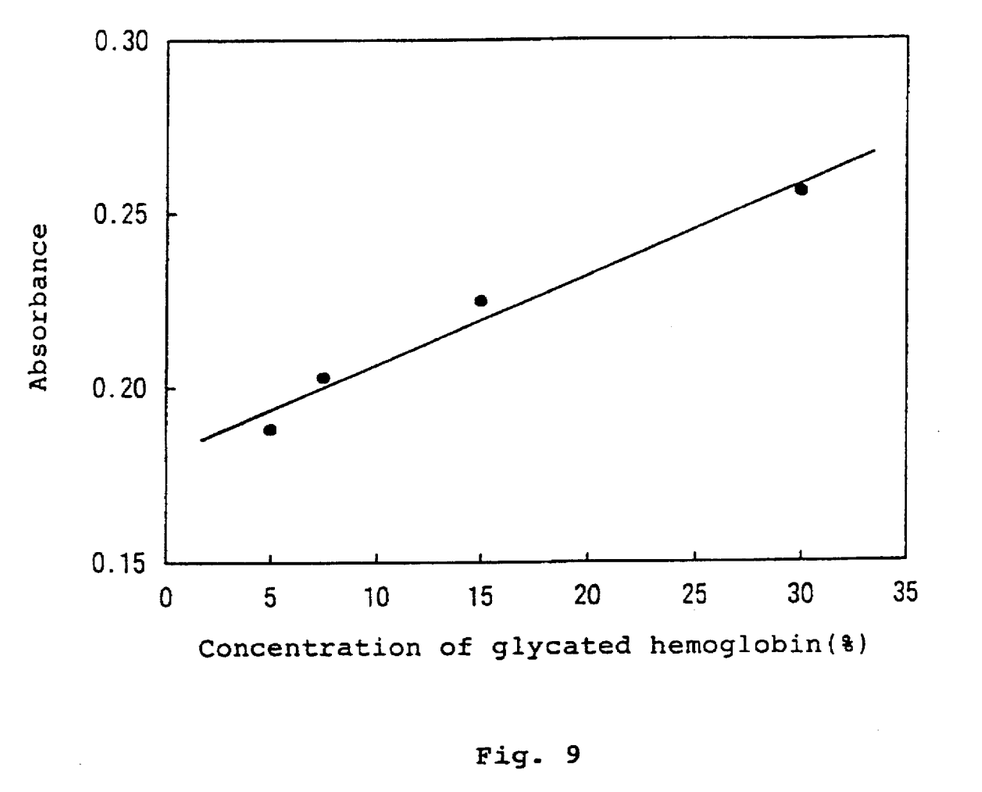
FIG. 9 is a graph illustrating a relation between concentration of the glycated hemoglobin and the amount of hydrogen peroxide produced due to FAOD action.

After combining the reagents, the total volume was adjusted to 1 ml with distilled water. FAOD-L solution (4 units/ml) was prepared by diluting the purified FAOD-L obtained in Example 1 with 0.1 M Tri-HCl buffer (pH 8.0). After incubating FAOD reaction mixture at 30° C. for 2 minutes, each of protease-treated solution (80 μl) was added thereto. Then, the absorbance at 727 nm after 30 minutes was measured to evaluate the relationships between the concentration of glycated hemoglobin and absorbance. The results are shown in FIG. 9, wherein the ordinate indicates the absorbance at 727 nm which corresponds to the amount of hydrogen peroxide generated and the abscissa indicates the concentration of glycated hemoglobin. FIG. 9 shows that the concentration of the glycated hemoglobin and the amount of hydrogen peroxide are correlated.

What is claimed is:

1. A fructosyl amino acid oxidase enzyme having the following physicochemical characteristics:

a) it catalyzes the oxidation of an amadori compound in the presence of oxygen to generate α-ketoaldehyde, amine derivatives and hydrogen peroxide;

b) it is active on fructosyl lysine and fructosyl valine, wherein the activity on fructosyl lysine is the same as or higher than the activity on fructosyl valine;

c) it is stable in the pH range of about 4.0 to 13.0 with optimal activity at a pH of 8.5;

d) it is stable in the temperature range of about 20° to 50° C. with optimal activity at a temperature of 30° to 35° C.;

e) the molecular weight is about 106,000 daltons when estimated by gel filtration with Superdex 200 pg;

f) a covalently-bound flavin adenine dinucleotide is required as a coenzyme for activity; and g) the isoelectric point of the enzyme is 6.8 as measured by disc electrofocussing.

2. The fructosyl amino acid oxidase enzyme of claim 1, which is obtained from a Fusarium species.

3. The fructosyl amino acid oxidase enzyme of claim 1, which is obtained from *Fusarium oxysporum* f.sp. lini, deposited as FERM BP-5792.

\* \* \* \* \*